(12) United States Patent
Jasko, III et al.

(10) Patent No.: US 9,546,395 B2
(45) Date of Patent: Jan. 17, 2017

(54) METHODS AND SYSTEMS FOR MONITORING BIOFILM GROWTH

(71) Applicants: Dow Global Technologies LLC, Midland, MI (US); Rohm and Haas Company, Philadelphia, PA (US)

(72) Inventors: Peter Jasko, III, Southampton, NJ (US); Robert Marquard, Ambler, PA (US); Christine Mcinnis, Blue Bell, PA (US)

(73) Assignees: ROHM AND HAAS COMPANY, Philadelphia, PA (US); DOW GLOBAL TECHNOLOGIES LLC, Midland, MI (US)

(*) Notice: Subject to any disclaimer, the term of this patent is extended or adjusted under 35 U.S.C. 154(b) by 168 days.

(21) Appl. No.: 14/571,641

(22) Filed: Dec. 16, 2014

(65) Prior Publication Data

US 2015/0167051 A1 Jun. 18, 2015

Related U.S. Application Data (60) Provisional application No. 61/883,613, filed on Dec. 16, 2013.

(51) Int. Cl.
| | | |
|---|---|---|
| *C12Q 1/66* | (2006.01) | |
| *G01N 1/16* | (2006.01) | |
| *B01F 3/04* | (2006.01) | |
| *C02F 1/00* | (2006.01) | |
| *C02F 103/02* | (2006.01) | |

(52) U.S. Cl.
CPC . *C12Q 1/66* (2013.01); *B01F 3/04* (2013.01); *C02F 1/008* (2013.01); *G01N 1/16* (2013.01); *C02F 2103/023* (2013.01); *C02F 2209/36* (2013.01); *C02F 2303/04* (2013.01); *C02F 2303/20* (2013.01)

(58) Field of Classification Search
CPC ............ C12Q 1/66; G01N 17/00; G01N 1/16; B01F 3/04; B01F 3/04078
USPC ................. 435/30; 261/110, 112.1
See application file for complete search history.

(56) References Cited

U.S. PATENT DOCUMENTS 5,049,492 A * 9/1991 Sauer ...................... G01N 1/02
422/538
2012/0085452 A1 4/2012 Thompson et al.

* cited by examiner

*Primary Examiner* — Robert A Hopkins
(74) *Attorney, Agent, or Firm* — Tifani M. Edwards (57) ABSTRACT

Systems and methods for monitoring biofilm growth are provided. A method comprises supporting at least one coupon in a water reservoir, wherein the water reservoir feeds water into a tower interior, removing the at least one coupon from the water reservoir, and measuring a level of biofilm growth on the at least one coupon. The level of biofilm growth on the at least one coupon is predictive of a level of biofilm growth within the tower interior. Providing an indicator of predictive biofilm growth may allow measures to be taken to prevent biofilm growth in other sectors or areas of the tower.

14 Claims, 5 Drawing Sheets

METHODS AND SYSTEMS FOR MONITORING BIOFILM GROWTH

BACKGROUND

Cooling towers are a widespread and effective heat transfer medium in industrial and utility type applications, thanks to the availability and high heat capacity of water. Cooling towers may be used to dissipate waste heat from air conditioning, industrial and power generation processes, among other uses. Proper maintenance of water quality within a cooling tower is important for the equipment to operate reliably, safely, and economically.

As water evaporates from the cooling tower and dissolved solids in the water begin to concentrate, there is a potential for microorganism growth. When microbial organisms reach a critical population, a slime layer or biofilm is formed. This slime layer contains both organic and inorganic matter. Some microorganisms excrete polymers and other protective substances which can encapsulate the microorganisms, protecting them from external environmental conditions. Biofilm growth generally occurs at interfaces between phases, for example, at an interface of air and water, and at an interface of water and a surface of the cooling tower.

As a result of biofilm formation, mixed populations of microorganisms can attach themselves to surface layers, causing the microorganisms to no longer be flushed away by cooling tower water flow and allowing for the growth of harmful bacteria, fungus, and macrobiota (e.g., protozoa including amoeba that support the growth of *Legionella*) that cannot otherwise survive in the bulk water. Biofilms protect microorganisms from disinfectants, causing water disinfection to be significantly more difficult when a biofilm is present. Within the protected biofilm layer, microorganisms can cause corrosion of the walls of the cooling towers and heat exchange systems. Moreover, biofilm creates an isolation layer on heat-exchange systems, causing them to no longer function properly and reduce efficiency in the heat exchanger, as well as blockage of filters, weirs, and screens in the system. The fill in a cooling tower can become so laden with biofilm that the entire cooling tower can collapse from the weight of the biofilm. Microorganisms present in the biofilm may accelerate oxygen uptake, causing an oxygen deficiency in the system. Some microorganisms may produce a number of organic acids, which causes a decrease in pH of the water in the cooling tower. Additionally, biofilms are a source of reinoculation (splash zones, dead spots, etc.) and reduced biocide performance. There are also potential health risks associated with biofilms in cooling water systems, such as *Legionella*, for example.

Reducing biofilm promotes the conservation of water, as more clean water is able to be recycled. Monitoring water quality improves the cycle number of water uses and reduces cooling system maintenance cost. Additionally, reducing biofilm on heat exchangers can also reduce the energy required to produce the same level of cooling.

Currently, it is common for service engineers to detect biofilm by sight or touch, at which point the biofilm is already well established. More scientifically robust methods are desired to detect biofilms before severe contamination occurs.

U.S. Patent Publication No. 2012/0085452 A1, published Apr. 12, 2012, discloses a corrosion coupon holder for fitting within a pipeline. However, monitoring and/or measurement of biofilm growth is different from monitoring and/or measurement of general corrosion not due to biofilm growth. Biofilm growth includes the adherence of live organisms to a coupon followed by extracellular polymeric substance (EPS) production and inorganic materials becoming entrapped in the biofilm EPS. Mature biofilm can be identified by the naked eye and scraped off of the coupon. Earlier stages of biofilm may be difficult to see by the naked eye, but organisms can be recovered from the surface of the coupon. Any corrosion resulting from the biofilm will be visible as deep pits form where galvanic cells were formed by the biofilm. While certain chemicals can create pitting corrosion, these pits will likely be more uniform in nature than the pitting corrosion from biofilm. The pitting corrosion from biofilm is generally not uniform in nature.

General corrosion is a uniform corrosion across the surface of the metal, and is measured differently from coupons. General corrosion is measured as the mil thickness of metal lost per year (mpy). When this measure is applied to any under deposit corrosion from biofilm, the mpy level is extremely low, even though there may be deep pits of corrosion. This is because metal is not being removed generally, but rather in specific locations. Thus, monitoring and measuring for biofilm growth and associated corrosion due to biofilm growth is different than monitoring and measuring for general corrosion that is not due to biofilm growth.

SUMMARY

In accordance with the present invention, methods and systems are defined for monitoring biofilm growth. In one embodiment, a method may comprise supporting at least one coupon in a water reservoir, wherein the water reservoir feeds water into a water based system interior, removing the at least one coupon from the water reservoir, and measuring a level of biofilm growth on the at least one coupon. The level of biofilm growth on the at least one coupon is predictive of a level of biofilm growth within the water based system. The water based system may comprise in one example embodiment a tower, such as a cooling tower. In other embodiments, the water based system may comprise a system for metalworking or pulp and paper processing. Providing an indicator of predictive biofilm growth may allow measures to be taken to prevent biofilm growth in other sectors or areas of the tower. Disinfecting the tower and its contents is easier when a biofilm is not present on surfaces in the tower, thus, providing predictive information regarding biofilm growth allows for easier maintenance of the tower.

In another embodiment, a system for cooling water is provided. The system comprises a cooling tower, a first conduit configured to transport fluid from a heat source to a distribution pan at a top of the cooling tower, a biofilm monitoring device positioned in the receiving pan, and a second conduit configured to transport cooled fluid out of the cooling tower.

In yet another embodiment, a biofilm monitoring device is provided. The device comprises a housing, wherein the housing comprises sidewalls and a bottom that define an interior, with holes extending through at least one of the sidewalls and the bottom to allow for fluid flow therethrough. The device further comprises at least one coupon rack, wherein the coupon rack is formed at least in part from a non corrosive material, and at least one biofilm monitoring coupon suspended on the at least one coupon rack within the interior.

These as well as other aspects and advantages of the synergy achieved by combining the various aspects of this technology, that while not previously disclosed, will become

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
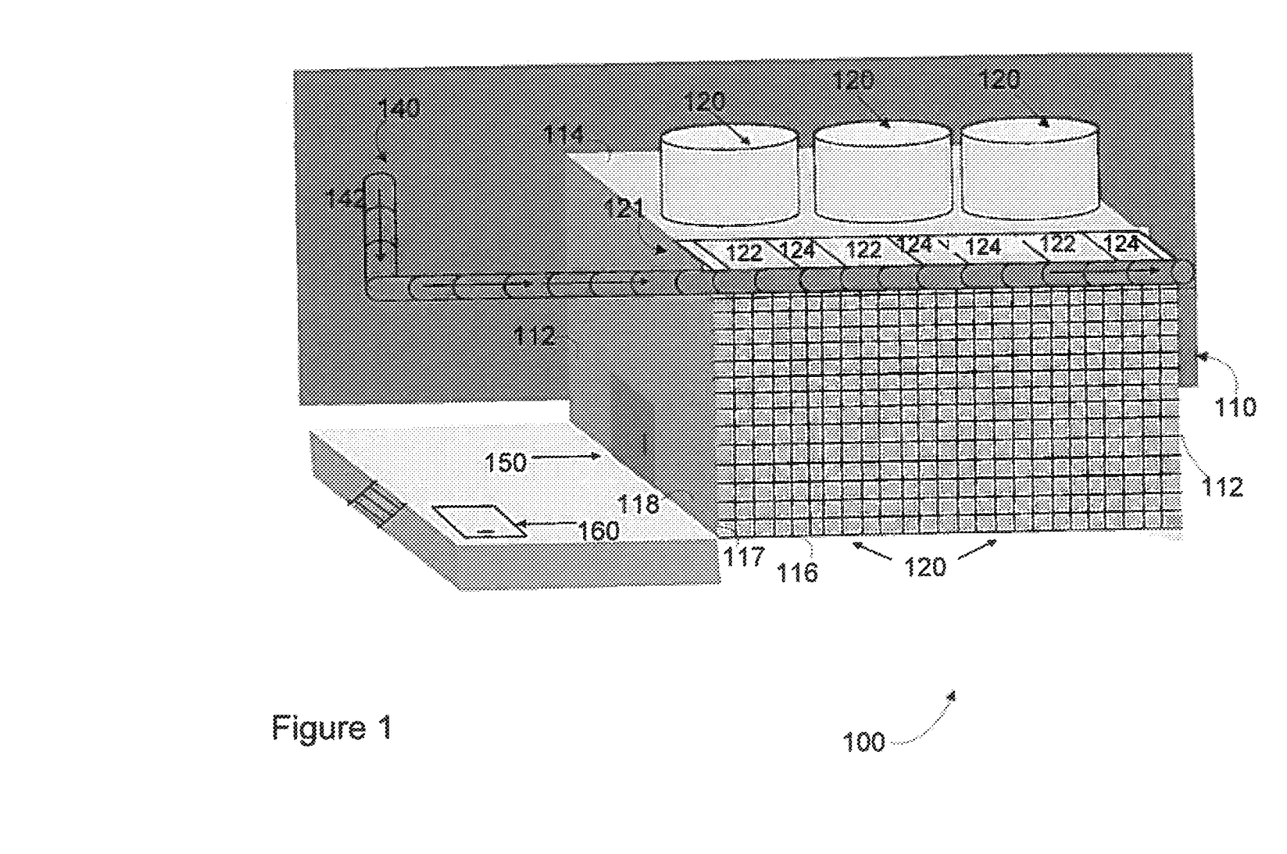
FIG. 1 depicts a schematic of an exemplary water cooling system in accordance with at least one embodiment.

FIG. 1 depicts a schematic of an exemplary water cooling system 100 in accordance with at least one embodiment. The water cooling system 100 is a heat removal system used to transfer process waste heat to the atmosphere. The water cooling system 100 may be used to dissipate waste heat from industrial, commercial, and power generation processes, and may be referred to as a system to handle industrial process water. Example systems that handle industrial process water include oil refineries, petrochemical and chemical plants, thermal power stations, and heating, ventilation, air conditioning (HVAC) systems, air washers, evaporative coolers, swamp coolers, brewery pasteurizers, can warmers, reverse osmosis systems, and pulp and paper applications. Other industrial process water or water based (like metalworking fluids) applications may also be envisioned.

FIG. 1 depicts a cross flow cooling tower design. In such a cross flow design, fans suck air from the atmosphere through the sides of the tower, through the fill, and out the top of the tower, cross flow to water falling down from the top of the tower to the bottom of the tower. In another example embodiment, fans may be placed on the sides of the tower to suck air across the tower horizontally while the water falls vertically from the top of the tower to the bottom of the tower.

The system 100 is connected to a heat source (not shown), such as one of the plants or systems discussed above, that produces heat by discharging hot fluids from equipment. Example equipment may comprise injection molding machines, air compressors, autoclaves, furnaces, mills, chillers, condensers, rollers, die casters, extruders, heat exchangers, oil coolers, welders, vacuum pumps, reactors and/or dehydration equipment. Other heat producing equipment may also be envisioned.

In FIG. 1, the system 100 may include a water based system, such as a tower 110 formed of a housing comprising sidewalls 112, a top 114, and a bottom 116, wherein the top 114 and the bottom 116 each comprise an interior surface 117 and an exterior surface 118. Tower fill 120 form at least one of the sidewalls 112 of the tower 110. The fill 120 shown is a splash type fill with supports, which generally comprise elongated bars in a configuration designed to disperse descending hot water. The fill 120 is configured to increase contact surface as well as contact time between air and water, allowing for better heat transfer. In some example embodiments, a film type fill may be used, wherein a series of thin, opposed sheets are configured to pass along descending water in a film.

A reservoir, or distribution pan 121 is present on the top 114 of the tower 119 having an apertured floor. The reservoir is a place where water collects and comprises low or inconsistent laminar flow. The distribution pan 121 may be segmented. Cells 122 are units comprising the distribution pan 121, fan 130, the fill 120, and a shared sump. Bays 124 comprise more than one segment of a distribution pan from a cell 122. Hot water from a water supply pipe 140 flows into the distribution pan 121, and the segments sort the water for flow through the apertured floor into the fill 120. The water in the distribution pan 121 may be referred to as tower return water 144. The tower return water is generally hot or warm, highly aerated water. This warm, aerated water provides a better environment for growing of microorganisms and fouls quicker than cooler, less aerated water.

Affixed to the exterior surface 118 of the top 114 of the tower 110 are tower fans 130. The fans 130 draw air through the sides of the tower 110 out into the atmosphere. The tower fans 130 may each comprise a mist eliminator.

The water supply pipe 140 brings water from a heat source, such as one of the example plants or systems described above, to the distribution pan 121. The direction of water flow is shown by arrows 142.

A first door 150 may be present on one of the sidewalls 112 that provides entry and access into the tower 110.

A second door 160 may be present with access to an area underneath the tower 110 to provide access to a sump (not shown). The sump may also be referred to as a basin or a water collection point. The water in the sump is relatively cool water, comprising a lower temperature than the hot or warm water that flows into the distribution pan 121.

In operation, a heat source discharges hot fluid, typically in the form of hot water or steam, from a condenser into the tower 110 via a pipe such as the water supply pipe 140. In some example embodiments, the hot fluid may be a coolant, and the water in the cooling tower may operate in a closed loop with respect to the industrial process. The hot fluid then is fed into the tower 110 via the distribution pan 121 and its associated cells and bays 122, 124, which distribute the descending fluid through the fill 120. As the fluid descends through the fill 120, crossflowing, cooling air intersects with the fluid, and a thermal interchange takes place between the cooling air and the hot fluid, effectively cooling the fluid. The cooled fluid may exit through an exit pipe at or near the bottom of the tower 110. Some of the cooled fluid may fall into the sump at the bottom of the tower. The cooled fluid exiting the tower 110 may then be returned to the plant for re-use.

Biofilm may grow on a number of surfaces within the cooling tower 110, as biofilm can grow on metal, concrete, and even plastic surfaces. Biofilm growth may even occur in the "splash zones" in the tower, where the sides of the tower are constantly wetted, but are not actually in contact with the water. The extracellular polymeric substance (EPS) present in biofilm is generally tacky and causes scale and corrosive products to stick to the biofilm. The combination of biofilm, scale, and corrosion products is termed biofouling, and leads to many problems in industrial process water systems, as previously discussed. Methods and associated devices and/or systems to monitor biofilm growth, especially to predict biofilm growth that may take place within a cooling tower such as tower 110, would be valuable to the efficient operation and management of such a tower and are discussed herein.

Figure 2:
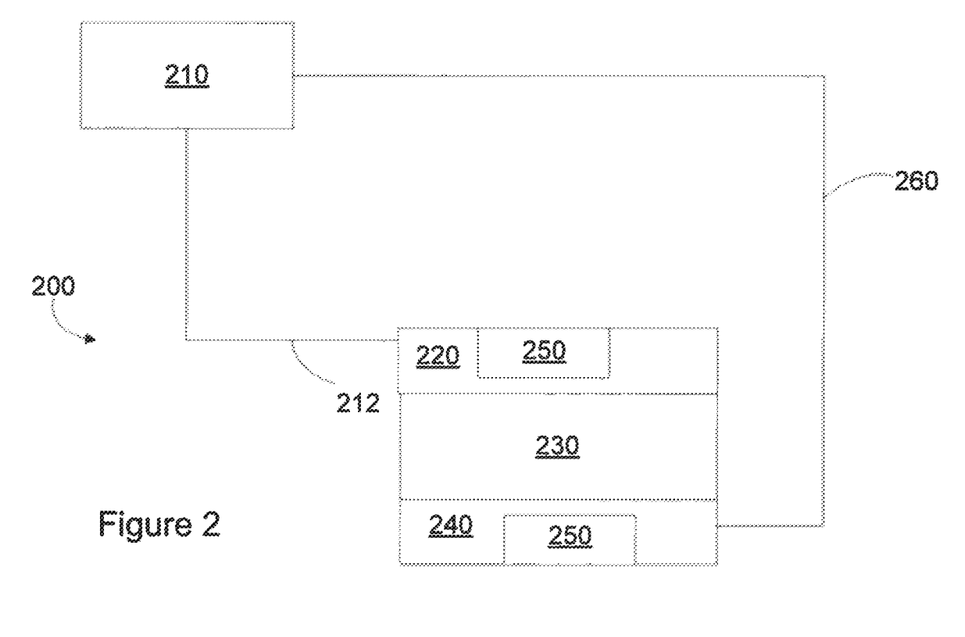
FIG. 2 depicts a schematic of an example monitoring system within a cooling loop, in accordance with at least one embodiment.

FIG. 2 depicts a schematic of an example monitoring system 200 within a cooling loop. Water flows from a heat source 210, such as one of the industrial plants described above, through one or more pipes 212, into a distribution pan 220 in a cooling tower 230, falls into a water collection basin or sump 240, and exits via an exit pipe 250 back to the heat source 210. The distribution pan 220 and the cooling tower 230 may be the same or similar to the distribution pan 121 and the cooling tower 110 described with reference to FIG. 1, in one example embodiment.

The monitoring system 200 comprises monitoring devices 250 positioned in water associated with the cooling tower 230 to provide predictive biofilm growth information for biofilm growth within the cooling tower. The location of the monitoring devices 250 allows for such predictive information to be obtained as the monitoring devices are strategically positioned in areas where biofilm growth occurs quicker than within the confines of the cooling tower. For example, when a monitoring device 250 is suspended in the distribution pan 220, the monitoring device 250 comes into contact with fluid that is warm and highly aerated. This warm, highly aerated water present in the distribution pan 220 provides a better environment for growing of microorganisms and fouls quicker than the water that cools as it proceeds to fall downstream through the distribution pan into the cooling tower 230. Thus, a monitoring device 250 in the distribution pan 220 may provide an indicator of predictive biofilm growth that may eventually occur in the cooling tower 230 should the present conditions of water through the cooling tower 230 remain the same. Some monitoring systems place monitoring devices in-line with the tower return water, for example, in the piping that transports water to and from the cooling tower. However, the level of aeration in the distribution pan is much higher than the water in-line with the tower return water.

A monitoring device 250 may also be suspended in a water collection basin at the bottom of the cooling tower 230, such as the sump 240. For example, a plastic coated cable may be used to suspend the monitoring device. The low flow of water in the sump 240 as compared to water descending through the cooling tower 220 allows for more biofilm growth in the sump 240, which may allow for quicker biofilm growth in the sump 240. Thus, a monitoring device 250 in the sump 240 may provide an indicator of predictive biofilm growth that may eventually occur in the cooling tower 230 should the present conditions of water through the cooling tower 230 remain the same.

Cooled water exits the cooling tower 230 and/or sump 240 via an exit pipe 260, and returns to the heat source 210 for additional use.

Figure 3:
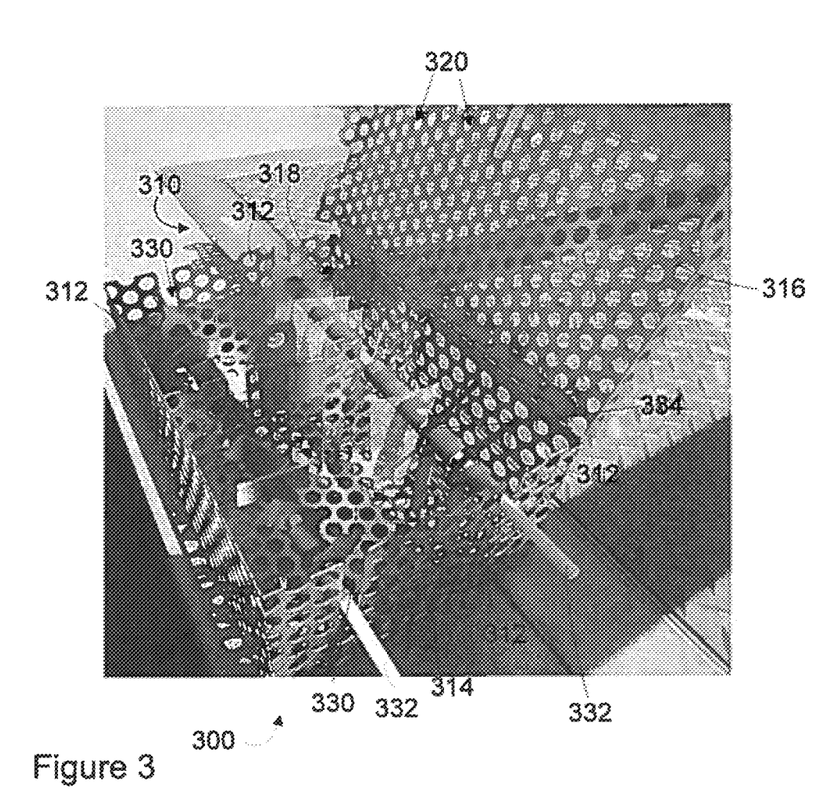
FIG. 3 depicts an example monitoring device for use with the water cooling system of FIG. 1 that may be placed in the cooling loop of FIG. 2.

FIG. 3 depicts an example monitoring device 300 for use with the exemplary system of FIG. 1 that may be used in a cooling loop 200 such as described with reference to FIG. 2.

Although the monitoring device 300 is described for use in a cooling tower system, in some example embodiments, the monitoring device 300 may be used with any industrial process water system. The monitoring device 300 may also be used in various other industrial processes that utilize water and/or other liquid material in processing steps, such as pulp and paper product making, reverse osmosis applications, and processes in the energy sector, such as those handling recovery fluids, for example. Example systems that handle industrial process water include oil refineries, petrochemical and chemical plants, thermal power stations, and heating, ventilation, air conditioning (HVAC) systems, air washers, evaporative coolers, swamp coolers, brewery pasteurizers, can warmers, reverse osmosis systems, and pulp and paper applications. Still other applications for monitoring biofilm in water based fluids, such as metalworking fluids, may be envisioned.

The monitoring device 300 comprises a metal cage 310 with four sidewalls 312, a bottom 314, and a top lid 316 that pivots about one or more hinges to open and close access into an interior 318 of the device 300. The top lid 316 may comprise a fastener or mating device to securely attach to a corresponding mating device on a sidewall 312 to close the lid 316. In some embodiments, the monitoring device 300 may not contain a top lid.

The sidewalls 312, bottom 314, and top lid 316 comprise a plurality of holes 320 to allow for fluid flow therethrough. Slits 330 are formed on two opposing sidewalls 312 to allow for placement of coupon racks 332, on which coupons 334 are threaded.

The sidewalls 312, bottom 314, and top lid 316 may be formed of metal sheeting. For example, the metal sheeting may comprise stainless steel, which is a corrosion resistant material. The holes 320 may be formed through the metal sheeting used to form the sidewalls 312, bottom 314, and top lid 316 via a punching process during manufacturing. In some example embodiments, the sidewalls 312, bottom 314, and top lid 316 may be formed of a plastic.

Each of the coupon racks 332 may be formed of an elongated member, for example, a pipe or bar, formed of a non corrosive material. In one example embodiment, the non corrosive material may comprise Teflon®. The coupon racks 332 may be spaced in parallel relationship within the monitoring device 300, as shown in FIG. 3. The coupon racks may be positioned to allow for layers of coupons to be placed within the monitoring device 300.

Coupon spacers 333 may be present on the coupon racks. The coupon spacers 333 may each comprise a larger diameter than the elongated member comprising the non corrosive material. The coupon spacers 333 may be formed of polyvinyl chloride (PVC) or another plastic to be positioned between and thus space apart coupons, preventing the coupons from hitting each other, and thus preventing mixed metal, or metal to metal, corrosion. Certain metals, when placed into contact, will corrode the metal with which they are in contact. Teflon® and PVC are non-corrosive and are able to withstand exposure to both the coupons and to fluid flow without significant deterioration. Additionally, such materials do not interact with the materials used for the coupons. Such materials are also cost effective and easy to machine and/or manufacture.

The level of aeration in the distribution pans is much higher than in the coupon rack installed in-line with the tower return water.

The coupons 334 may be hung or otherwise suspended on the coupon racks 332, as shown in FIG. 3. A hole in a coupon 334 may be sized and shaped to allow for the hole to be threaded on or over a pipe comprising the coupon rack 332. The coupons may be made from steel, aluminum, copper, plastic, or glass, for example. Solid coupons or mesh coupons may be used. Other example coupons suitable for monitoring and/or measuring biofilm growth may be envisioned.

When the monitoring device 300 is placed within fluid, such as water, in a cooling tower system, at least a portion of one or more coupons 332 in the monitoring device 300 is exposed to the fluid. In some example embodiments, only a portion of the coupons 332 may be exposed to the water. For example, the coupons 332 may be only partially submerged and thus part of the coupons 332 will only receive spray from the water; this mimics and thereby allows for an understanding of biofilm growth that may occur in a splash zone within the cooling tower, where a tower surface receives only spray from the water. Thus, the partially submerged coupons may be monitored and/or measurements obtained to determine biofilm growth on the non-submerged portions of the coupons.

If the monitoring device 300 is placed in a distribution pan such as the distribution pans 121 or 220 of FIGS. 1 and 2, the top lid 316 of the monitoring device 300 may remain above the top surface of water present within the distribution pan or there may not be a top lid as a top part of the monitoring device 300 may remain above the top surface of the water, whereas the bottom 314 may be submerged in the water.

In another example embodiment, if the monitoring device 300 is placed in a sump of a cooling tower system, the entire monitoring device 300 may be submerged under water within the sump. The monitoring device 300 may be suspended, either partially or fully, under water, using any of a number of suspension methods and systems. For example, a roping system may be used to suspend the monitoring device 300. The monitoring device 300 is preferably suspended so that the monitoring device does not sit on the floor of the sump as the sump floor is generally full of collected debris such as leaves, dirt, scale and corrosion products, and other organic and inorganic sludge.

Bacteria carried in the fluid will adhere to and grow on the surface of a coupon 334 that comes into contact with the fluid. The monitoring device 300 may later be removed from the fluid, the coupons 334 may be removed from the monitoring device 300 for examination and analysis for biofilm growth. In one example, visual measurement or analysis may be performed to observe an amount of growth on the coupons 334. In another example, the coupons 334 may be subjected to further analysis, such as described in reference to FIG. 4, for quantitative measurements.

Example 1

Measuring Levels of Biofilm Growth

Figure 4:
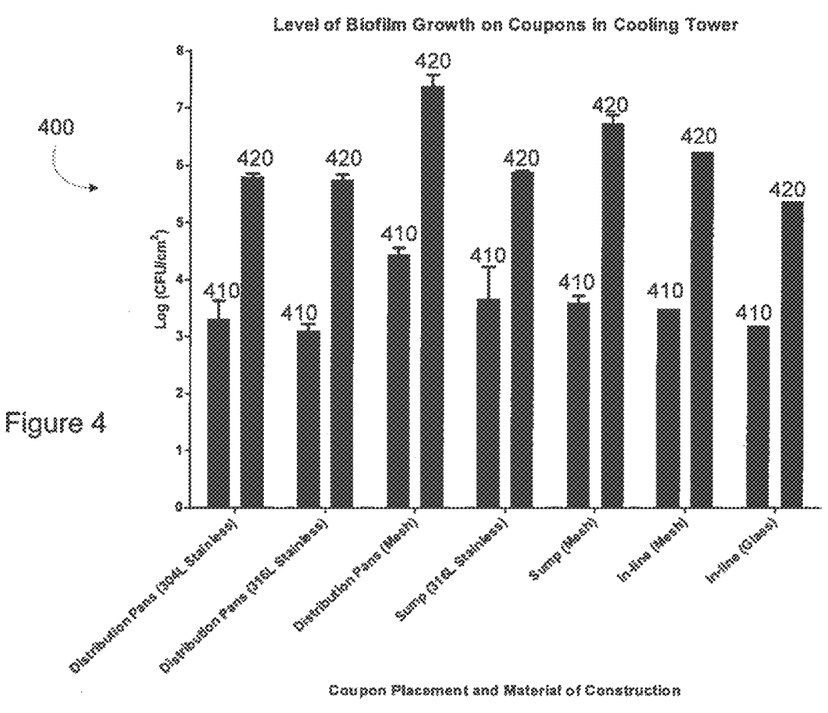
FIG. 4 depicts a graph illustrating level of biofilm growth on coupons in a cooling tower plotted over coupon placement and material of construction, as may be determined using the water cooling system of FIG. 1 in accordance with at least one embodiment.

FIG. 4 depicts a graph illustrating levels of biofilm growth on coupons in a cooling tower plotted over coupon placement and material of construction, as may be determined using the example system of FIG. 1, in accordance with at least one embodiment.

For Example 1, biofilm was measured in a 100,000 gallon system volume induced flow cooling tower. Such a cooling tower may be the same as or similar to the cooling tower system 100 described with reference to FIG. 1, for example.

Coupons were made of aluminum mesh (Phifer Brite Aluminum Screen), solid stainless steel (Metal Samples, a Branch of Alabama Specialty Products, Inc.) comprising alloys 304L and 316L, or glass. The coupons were placed in a monitoring device such as the monitoring device 300 described with reference to FIG. 3, and the monitoring device was then suspended just below the water surface in the cooling tower's distribution basin, or was suspended one foot below the water surface in the sump of the cooling tower. Additionally, some coupons were placed in a Nalco Biobox which was placed in-line with the tower return water. The dimensions of the coupons tested are provided in Table 1, below. Multiple coupons of each type were placed in each of the three locations described above to measure reproducibility.

TABLE 1

| Coupon Type | Dimensions (Length × Width) (cm) | Surface Area ($cm^2$) |
| --- | --- | --- |
| Stainless steel | 5 × 1.9 | 19 |
| Aluminum Mesh in the Sump | 7.5 × 5 | 75 |
| Aluminum Mesh in the Distribution Pans | 10 × 5 | 100 |
| Glass Slides | 7.5 × 2.5 | 37.5 |

Upon removal from the testing locations, the coupons were immersed in 100 mL of phosphate buffer with $MgCl_2$. Biofilm was removed from the coupons by a combination of scraping the biomass off of the coupons with a rubber policeman, sonicating the coupons, and a vigorous shaking to remove and suspend the biomass. Solutions of the phosphate buffer contaminated with biomass from the coupons were vigorously mixed before sampling. Additionally, the results were normalized to the surface area of the coupon, as not all coupons were the same size (this can be seen in Table 1).

The coupons were then analyzed using two methods. The first method was most probable number (MPN) enumeration. The number of colony forming units per millimeter (CFU/mL) in the samples was determined by using an MPN statistical method combined with a microtiter plate system. Trypticase Soy Broth was used as the growth media for this example experiment. After the biofilm was removed from the coupons, 20 µL of each sample was transferred by pipette to the first column of the first four rows of the 96-well microtiter plate used for MPN enumeration. Two biofilm samples were tested per plate. An automated workstation, the Biomek 2000, was used to make serial dilutions of each plate. The plates were then incubated in the 30° C. incubator for forty-eight hours. After incubation, the plates were read by determining the number of wells in each column containing microbial growth. Microbial growth was determined by wells that were turbid as opposed to transparent wells which contained no microbial growth. Statistical tables were used to calculate the most probable number estimate of the microbial population of the sample from a combination of positive growth readings in the 96 well plate.

The second method was using adenosine triphosphate (ATP) analysis. Cellular Adenosine Triphosphate (cATP) was determined using LuminUltra Technologies, Ltd.'s test kit, Quench Gone Aqueous (QGA). The QGA method is a filtration-based analysis which measures ATP based on the firefly luminase assay. ATP reacts with the enzyme luciferase, produced by the firefly, to produce light which is measured on a luminometer. One milliliter of the phosphate buffer biofilm suspension was passed through a syringe filter to concentrate the microorganisms. ATP was extracted from the microorganisms caught on the filter and the extract was diluted prior to measuring on the luminometer. The concentration of cellular ATP in the samples was calculated relative to the concentration of cellular ATP in the UltraCheck 1 calibration standard.

Although the methods MPN and ATP were used in Example 1, other methods for measurement of biofilm may be envisioned. For example, methods for analyzing biofilm growth such as plate counts, dissolved oxygen uptake, and HMB/catalase may be used.

FIG. 4 is thus a comparison of the number of organisms per $cm^2$ for biofilm monitoring coupons with respect to cooling tower location and coupon material. In Example 1, all of the coupons were placed in the cooling tower over the same period of time. The bars 410 represent data obtained from experiments using the MPN method of analysis, and the bars 420 represent data obtained from experiments using the ATP method of analysis.

From FIG. 4, the highest level of biofilm was detected in the distribution pans using mesh coupons. The distribution pans contain the same warm water as the tower return water. However, the level of aeration in the distribution pans is much higher than in the coupon rack installed in-line with the tower return water. The warm water coupled with the high levels of aeration allows for the best biofilm growth. The mesh coupon may modify the flow over the coupon in such a way that the shearing forces are reduced, providing a favorable environment for microbes to attach to the mesh coupon and form a biofilm. Because the water in the distribution pans provides the most favorable conditions for microbe growth, other areas of the cooling tower may not experience the same level of biofilm growth. Thus, installing a monitoring device in the distribution pans may be a predictor of the tendency of the cooling tower to have a biofilm problem, and may not represent the actual level of biofilm within the tower. Such a predictor could be helpful in prevention of a biofilm problem in the cooling tower. As discussed above, current methods show a biofilm issue once it has already become a problem, and amelioration of the problem is, at that stage, more difficult and costly. A predictive indicator of biofilm growth is advantageous to prevent a biofilm problem from arising within the cooling tower, and reduce the cost of biofilm remediation.

As shown in FIG. 4, the higher level of growth on the mesh coupons in the distribution pans was found by both the MPN and the ATP methods of analysis. The ATP method found about two orders of magnitude more microorganisms than the MPN method in all cases tested. This is likely because the ATP method is able to detect organisms that may not be culturable in laboratory growth media, or because the biofilm may contain organisms with higher levels of ATP per cell than was estimated for a pure bacterial culture.

Figure 5:
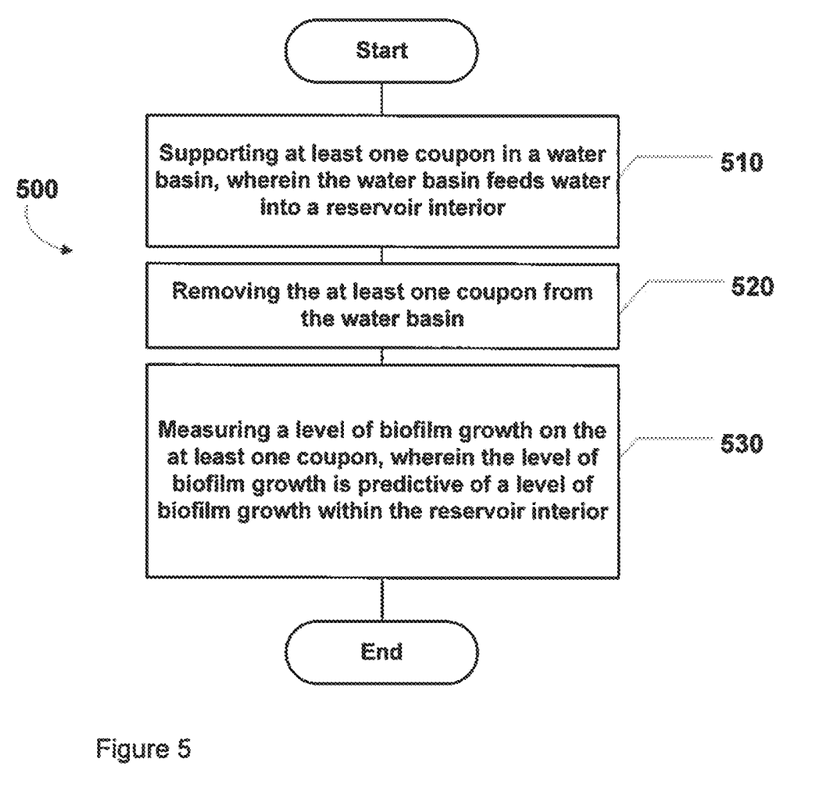
FIG. 5 depicts a simplified flow diagram of an example method that may be carried out to monitor biofilm growth, in accordance with at least one embodiment.

FIG. 5 depicts a simplified flow diagram of an example method 500 that may be carried out to monitor biofilm growth, in accordance with at least one embodiment. Method 500 shown in FIG. 5 presents an embodiment of a method that, for example, could be used with the system 100 and/or the cooling loop 200.

In addition, for the method 500 and other processes and methods disclosed herein, the flowchart shows functionality and operation of one possible implementation of the present embodiments.

Initially, the method 500 includes supporting at least one coupon in a water reservoir, wherein the water reservoir feeds water into a tower interior, at block 510. The water reservoir may be the same or similar to the distribution pans or basins 121 or 220 of FIGS. 1 and 2, in one example embodiment, or may be the same or similar to the sump 240 of FIG. 2. The tower may be the cooling tower 110 or 230 of FIGS. 1 and 2, for example.

The method 500 then includes removing the at least one coupon from the water reservoir, at block 520. The at least one coupon may be suspended within a monitoring device such as the monitoring device 300 of FIG. 3.

The method 500 includes measuring a level of biofilm growth on the at least one coupon, wherein the level of biofilm growth is predictive of a level of biofilm growth within the tower interior, at block 530. A number of methods of measurement may be used. For example, the methods described in Example 1 with reference to FIG. 4 may be used, such as ATP and MPN. In another example embodiment, measuring may comprise a visual analysis of the amount of biofilm growth on the at least one coupon. A visual comparison of the amount of biofilm growth may be conducted over time, wherein the biofilm coupon is checked at regular intervals of time to monitor and visually compare biofilm amounts on the at least one coupon at the expiration of each time interval.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method for monitoring biofilm growth comprising:
   supporting at least one coupon in a water reservoir, wherein the water reservoir is in fluid communication with a water based system interior;
   removing the at least one coupon from the water reservoir; and
   measuring a level of biofilm growth on the at least one coupon;
   wherein the level of biofilm growth is predictive of a level of biofilm growth within the water based system interior
   wherein the water reservoir is a distribution pan and the water based system is a cooling tower.

2. The method of claim 1, further comprising:
   transporting hot water from a heat source to the distribution pan via a pipe, wherein the hot water in the distribution pan is highly aerated.

3. The method of claim 2, wherein the hot, aerated water in the distribution pan promotes biofilm growth faster than the water moving through the water based system interior.

4. The method of claim 1, further comprising:
   the water reservoir receiving water from the water based system interior, wherein the water reservoir is a sump and the water based system is a cooling tower, and wherein a water flow rate in the sump is lower than a water flow rate through the water based system interior.

5. The method of claim 1, wherein supporting at least one coupon in in a reservoir comprises hanging the at least one coupon on an elongated member comprised of a non corrosive material within an interior of a cage through which fluid flows.

6. A system for cooling fluid, comprising:
   a cooling tower;

a first conduit configured to transport fluid from a heat source to a distribution pan at a top of the cooling tower, wherein the fluid flows through apertures in a bottom of the distribution pan into the cooling tower;

a biofilm monitoring device positioned in the distribution pan to indicate biofilm growth within the basin; and a second conduit configured to transport cooled fluid out of the cooling tower.

7. The system of claim 6, further comprising:

a second biofilm monitoring device positioned in a water collection basin underneath and in fluid communication with the cooling tower.

8. The system of claim 6, wherein the biofilm monitoring device further comprises:

a housing, comprising sidewalls and a bottom that define an interior, with holes extending through at least one of the sidewalls and the bottom;

at least one biofilm monitoring coupon within the interior.

9. The system of claim 8, wherein when the biofilm monitoring device is positioned in the distribution pan at least a portion of the at least one biofilm monitoring coupon is in contact with the fluid.

10. The system of claim 6, wherein the distribution pan comprises water that has a higher temperature and aeration than water flowing through the cooling tower.

11. The system of claim 10, wherein the biofilm monitoring device in the distribution pan indicates a predictive biofilm growth for water in the cooling tower as biofilm growth is quicker in the basin than in the cooling tower.

12. A biofilm monitoring device, comprising:

a housing, wherein the housing comprises sidewalls and a bottom that define an interior, with holes extending through at least one of the sidewalls and the bottom to allow for fluid flow therethrough;

at least one coupon rack, wherein the coupon rack is formed at least in part from a non corrosive material;

at least one biofilm monitoring coupon suspended on the at least one coupon rack within the interior.

13. The biofilm monitoring device of claim 12, wherein the at least one coupon rack is formed of the elongated member comprised of the non corrosive material with polyvinyl chloride (PVC) spacers to separate the one or more coupons.

14. The biofilm monitoring device of claim 12, wherein the device comprises at least two coupon racks placed in parallel relationship to each other.

* * * * *